United States Patent
Perkins et al.

(10) Patent No.: US 8,368,540 B2
(45) Date of Patent: *Feb. 5, 2013

(54) WIRELESS TRACKING SYSTEM AND METHOD UTILIZING NEAR-FIELD COMMUNICATION DEVICES

(75) Inventors: Matthew R. Perkins, San Diego, CA (US); Anthony Truscott, San Diego, CA (US)

(73) Assignee: Awarepoint Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/527,563

(22) Filed: Jun. 19, 2012

(65) Prior Publication Data

US 2012/0264374 A1    Oct. 18, 2012

Related U.S. Application Data

(63) Continuation of application No. 12/855,509, filed on Sep. 18, 2010.

(60) Provisional application No. 61/244,053, filed on Sep. 20, 2009.

(51) Int. Cl.
*G08B 13/14* (2006.01)
*H04Q 5/22* (2006.01)
*H04B 7/00* (2006.01)
*G06Q 10/00* (2012.01)

(52) U.S. Cl. ........... 340/572.1; 340/539.12; 340/539.13; 340/541; 340/10.1; 455/41.1; 455/41.2; 455/423; 455/426.2; 455/67.11; 705/2; 705/3

(58) Field of Classification Search .......... None
See application file for complete search history.

(56) References Cited

U.S. PATENT DOCUMENTS

| | | | |
|---|---|---|---|
| 5,732,401 A | 3/1998 | Conway | |
| 5,812,865 A * | 9/1998 | Theimer et al. | 709/228 |
| 5,977,913 A | 11/1999 | Christ | |
| 7,123,149 B2 | 10/2006 | Nowak et al. | |
| 7,197,326 B2 * | 3/2007 | Acampora | 455/522 |
| 7,312,752 B2 | 12/2007 | Smith et al. | |
| 7,324,824 B2 | 1/2008 | Smith et al. | |
| 7,471,200 B2 * | 12/2008 | Otranen | 340/572.1 |
| 2005/0021369 A1 | 1/2005 | Cohen et al. | |
| 2006/0055552 A1 | 3/2006 | Chung et al. | |
| 2006/0056363 A1 | 3/2006 | Ratiu et al. | |
| 2008/0012767 A1 | 1/2008 | Caliri et al. | |
| 2008/0068267 A1 | 3/2008 | Huseth et al. | |
| 2008/0081608 A1 | 4/2008 | Findikli et al. | |
| 2008/0133127 A1 | 6/2008 | Havens | |
| 2009/0069642 A1 | 3/2009 | Gao et al. | |

FOREIGN PATENT DOCUMENTS

WO    WO2009045085    4/2009
WO    WO2009066951    5/2009

OTHER PUBLICATIONS

International Search Report and Written Opinion for PCT Application No. PCT/US2010/049413, Priority Date Sep. 20, 20009, filed on Sep. 18, 2010 and Date of completion May 20, 2011.

* cited by examiner

*Primary Examiner* — Wayne Young
*Assistant Examiner* — Fekadeselassie Girma
(74) *Attorney, Agent, or Firm* — Clause Eight IPS; Michael Catania

(57) ABSTRACT

The present invention provides a method and system to determining a near-field communication interaction in a wireless tracking mesh network. The present invention preferably utilizes near-field communication devices in conjunction with tracking tags to transmit signals for reception by sensors stationed throughout a facility which form a mesh network and forward the signals to an information engine for analysis.

17 Claims, 8 Drawing Sheets

WIRELESS TRACKING SYSTEM AND METHOD UTILIZING NEAR-FIELD COMMUNICATION DEVICES

CROSS REFERENCES TO RELATED APPLICATIONS

The present application is a continuation application of U.S. patent application Ser. No. 12/885,509, filed on Sep. 18, 2010, which claims priority to U.S. Provisional Patent Application No. 61/244,053, filed Sep. 20, 2009, now abandoned, both of which are hereby incorporated by reference in their entireties.

STATEMENT REGARDING FEDERALLY SPONSORED RESEARCH OR DEVELOPMENT

Not Applicable

BACKGROUND OF THE INVENTION

1. Field of the Invention

The present invention is related to wireless tracking systems and methods utilizing near-field communication devices. More specifically, the present invention relates to a system and method utilizing near-field communication devices for analyzing near-field communication interactions.

2. Description of the Related Art

Real-time knowledge of resources, whether the resources are assets or people, is becoming a necessary tool of many businesses. Real-time knowledge of the location, status and movement of crucial resources can allow a business to operate more efficiently and with fewer errors. However, many businesses employ hundreds if not thousands of resources in a single facility, and these resources need to be accounted for by a central system that is user friendly.

For example, in a typical hospital there are numerous shifts of employees that utilize the same equipment. When a new shift arrives, the ability to quickly locate medical equipment not only results in a more efficient use of resources, but also can result in averting a medical emergency. Thus, the tracking of medical equipment in a hospital is becoming a standard practice.

The tracking of objects in other facilities is rapidly becoming a means of achieving greater efficiency. A typical radio frequency identification system includes at least multiple tagged objects, each of which transmits a signal, multiple receivers for receiving the transmissions from the tagged objects, and a processing means for analyzing the transmissions to determine the locations of the tagged objects within a predetermined environment. Further, the ability to not only track but analyze resources would further improve efficiencies.

The prior art discloses various tracking systems and uses of near-field communication devices. Near field communication typically operates in the 13.56 MHz frequency range, over a distance of one meter or less and usually a few centimeters. Near field communication technology is standardized in ISO 18092, ECMA 340, and ETSI TS 102 190.

One reference discloses an adapter for a tag that is configured to emulate a near filed communication reader-to-reader tag.

Another reference discloses a medical diagnostic system that includes a data acquisition device having a near field communication device for transfer of data.

Still another reference discloses using ECMA 340 standard for near field communication.

Another reference discloses a system for monitoring a patient that uses a personal status monitoring device, such as an ECG electrode assembly, which transmits a signal to an intermediary device, such as a PDA, which transmits to a server using a WLAN.

Another reference discloses an object identifier that transmits both an IR signal and a RF signal for location determination.

Another reference discloses a system which allows for a location to be determined without requiring precise calculations through use of an object identifier that transmits one identifier corresponding to an object identifier and a second identifier which is a group identifier.

Another reference discloses a system for recording object associations based on signals for object identifiers.

Another reference discloses a system that uses NFC technology to determine a secondary transport mechanism.

Another reference discloses a system that uses BLUETOOTH technology integrated in a cellular telephone to provide interpersonal communications between individuals.

Another reference discloses near field communication devices that determine an efficient protocol for sharing information.

Another reference discloses passing advertising messages to a mobile client using near field communication technology.

As stated above, the problem is inadequate resource visibility in a business. Businesses such as hospitals, need to locate resources (assets and people), know the status of the resources, and understand the usage history of the resources to enable business improvement.

Specific problems for hospitals include tracking infections in a hospital to determine a source and other areas or individuals that may be infected. Other problems include spotting emerging patterns of infection and outbreaks to mitigate those affected. Further, for MEDICARE and other insurance providers, hospitals and other medical facilities need to demonstrate that patients received their required care in order to receive payment for such care. The prior art has failed to provide an adequate solution to these problems.

Further, there is a need in the health care market to determine when interactions occur between patient worn devices and clinician worn devices. Being able to detect this interaction will drive many applications that revolve around workflow, patient flow and asset tracking To enable the detection of these interaction events, a communication protocol must be defined such that the tags will recognize when they are in-range of each other and report on the in-range event. Off-the-shelf technologies can be employed for this use case but the battery-life, communication range and data rate requirements are often traded for communication performance. For example, peer-to-peer WiFi could be used to establish a near-real time connection between two devices but the battery life of the WiFi-enabled device would be on the order of 1-2 days which would not support the application need. Many other technologies have the same drawbacks.

To accomplish these applications, one must find a system that doesn't trade battery life for response time, or communication distance for battery life.

BRIEF SUMMARY OF THE INVENTION

The present invention provides a solution in the form of a low-power interaction detection circuit that triggers a higher-power communication system that can transfer more meaningful data after an interaction event has been detected. The solution determines a near-field communication interaction between objects through wireless tracking. The present invention utilizes near-field communication devices attached to objects (including individuals) and the objects also have the capability to transmit signals for reception by sensors stationed throughout a facility which forward the signals to an information engine for analysis of a near-field communication interaction.

One aspect of the present invention is a system for monitoring interaction data for multiple users and objects utilizing near-field communication devices in an indoor facility through a medium range wireless communication format and a short range wireless communication format. The system includes a mesh network, a plurality of near-field communication devices and an information engine. Each of the plurality of near-field communication devices transmits a beacon signal using a short range wireless communication format receivable by another near-field communication device when the near-field communication devices are within physical proximity of each other. At least one of the near-field communication devices transmits interaction data using a medium range wireless communication format to the mesh network. The information engine is in communication with the mesh network and processes the interaction data.

The medium range wireless communication format is preferably selected from ZIGBEE communication format, Bluetooth communication format, Low-Power BlueTooth communication format, WiFi communication format, Low-Power WiFi communication format, Ultra Wide Band communication format, Ultrasound communication format or Infrared communication format. The short range wireless communication format is preferably selected from a near-field communication format, a low frequency communication format or a magnetic field communication format. Alternatively, the short range wireless communication format is selected from a magnetic induction communication format, 9 kHz communication format, <125 kHz communication format, 125 kHz RFID communication format, 13.56 MHz communication format, 433 MHz communication format, 433 MHz RFID communication format, or 900 MHz RFID communication format.

Another aspect of the present invention is a system for determining a business relationship between individuals within a facility. The system includes multiple near-field communication devices, multiple tags, a mesh network and an information engine. The mesh network is preferably an 802.15.4 ZIGBEE wireless sensor network. Each of the first near-field communication devices represented is associated with an individual. Each of the tags represents an object. The mesh network includes multiple plug-in sensors located within the facility. The information engine is in communication with the mesh network. The information engine determines a business relationship between a first bearer and a second bearer having a near-field communication interaction based on at least two of multiple factors which include a position location of the interaction, a duration of the interaction, a previous location of the first bearer, a previous location of the second bearer and the number of other objects located near the near-field communication interaction.

In a preferred embodiment, the plurality of factors further includes a position designation of the first person and a position designation of the second person and a number of previous interactions between the first person and the second person within a predetermined time period.

Another aspect of the present invention is a method for determining a business relationship between individuals within a facility. The method includes transmitting a signal from a tag associated with a first person, and the signal comprises data about a near-field communication interaction between the first person and a second person. The method also includes receiving the signal from the first tag at a mesh network established within the facility. The method also includes determining that an interaction is occurring between the first person and the second person. The method also includes determining a business relationship between the first person and the second person based on multiple factors. The multiple factors can include a position location of the interaction, a duration of the interaction, a previous location of the first person prior to the interaction, a previous location of the second person prior to the interaction, a position designation of the first person and a position designation of the second person, a number of previous interactions between the first person and the second person within a predetermined time period, and the number of other persons at the interaction.

Yet another aspect of the present invention is a system for determining a business relationship between individuals within a facility. The system includes multiple near-field communication devices, multiple tags, a mesh network and an information engine. Each of the near-field communication devices is associated with an individual person. Each of the tags represents a first object. The mesh network includes multiple plug-in sensors located within the facility. The information engine is in communication with the mesh network. The information engine analyzes a near-field communication interaction. The multiple factors for the near field communication interaction include a position location of the interaction, a duration of the interaction, a previous location of the first person prior to the interaction, and information for a mobile object within a predetermined distance of the location of the interaction.

In one example, the information engine analyzes the near-field communication interaction to determine a billing charge for services of the first person. In another example, the facility is a hospital and the information engine analyzes the near-field communication interaction to determine medical services provided to a patient.

Yet another aspect of the present invention is a system for analyzing an action of an individual. The system includes near-field communication devices, tags, a mesh network and an information engine. Each of the near-field communication devices is associated with an individual person. Each of the tags is associated with a mobile object. The mesh network includes multiple sensors positioned within a facility. The mesh network receives transmissions from each tags and each of the near-field communication devices. The information engine is in communication with the mesh network. The information engine analyzes near-field communication interactions between individuals. The information engine further analyzes an action of a first person based on a plurality of factors including a position location of the action, a duration of the action, a previous location of the first person prior to the action, and information for a mobile object within a predetermined distance of the location of the action.

Each communication device preferably has a low-power, short-range (<1 foot) communication feature that can detect the presence, or absence, of a signal from another device. Short bits of information are preferably exchanged (<256 bits) between devices but such an exchange is not mandatory. RFID systems operating at frequencies of sub-125 kHz, 125 kHz, 433 MHz, 900 MHz, or 2.4 GHz are used with the present invention. The communication devices alternatively transmit at frequencies as low as 5 kiloHertz ("kHz") and as high as 900 MegaHertz ("MHz"). Other frequencies utilized by the tags for a low-power short-range communication system include 9 kHz, <125 kHz, 433 MHz, and 900 MHz.

Each device preferably contains a low-power, medium-range (1 foot to 30 feet) wireless communication system. Such wireless communication systems include ZIGBEE, BLUETOOTH, Low-Power BLUETOOTH, WiFi or Low-Power WiFi, Ultra Wide Band ("UWB"), Ultrasound and Infrared communication systems. The wireless communication system is used to exchange device specific information after the low-power short-range system has indicated that an interaction has occurred. Those skilled in the pertinent art will recognize that the wireless communication system can also be used independent of the low-power short-range system for other wireless communication applications such as location and tracking, sense and control, building automation, smart energy, telecom applications, consumer building automation, remote control applications, home health care, personal fitness, personal wellness, and many other applications.

Each communication device preferably continuously transmits a beacon signal using the short-range communication protocol. When a beacon signal is received by another communication device, the receiving communication device can respond using the low-power communication circuit and/or it can respond using the medium-power protocol. The medium-power communication system can transfer larger data packets at a higher transmission rate. Data that might be included in a medium-power transmission include device ID, time stamp, location information, user information, software version, and/or protocol version. A medium-power transmission is preferably acknowledged when received by the receiving communication device. Further, at this point either communication device, or both communication devices, can transmit the information from the interaction to the medium-power infrastructure or to a neighboring communication device. Additionally, the communication devices may also elect to store the interaction information and download/transmit the interaction information at a later time.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
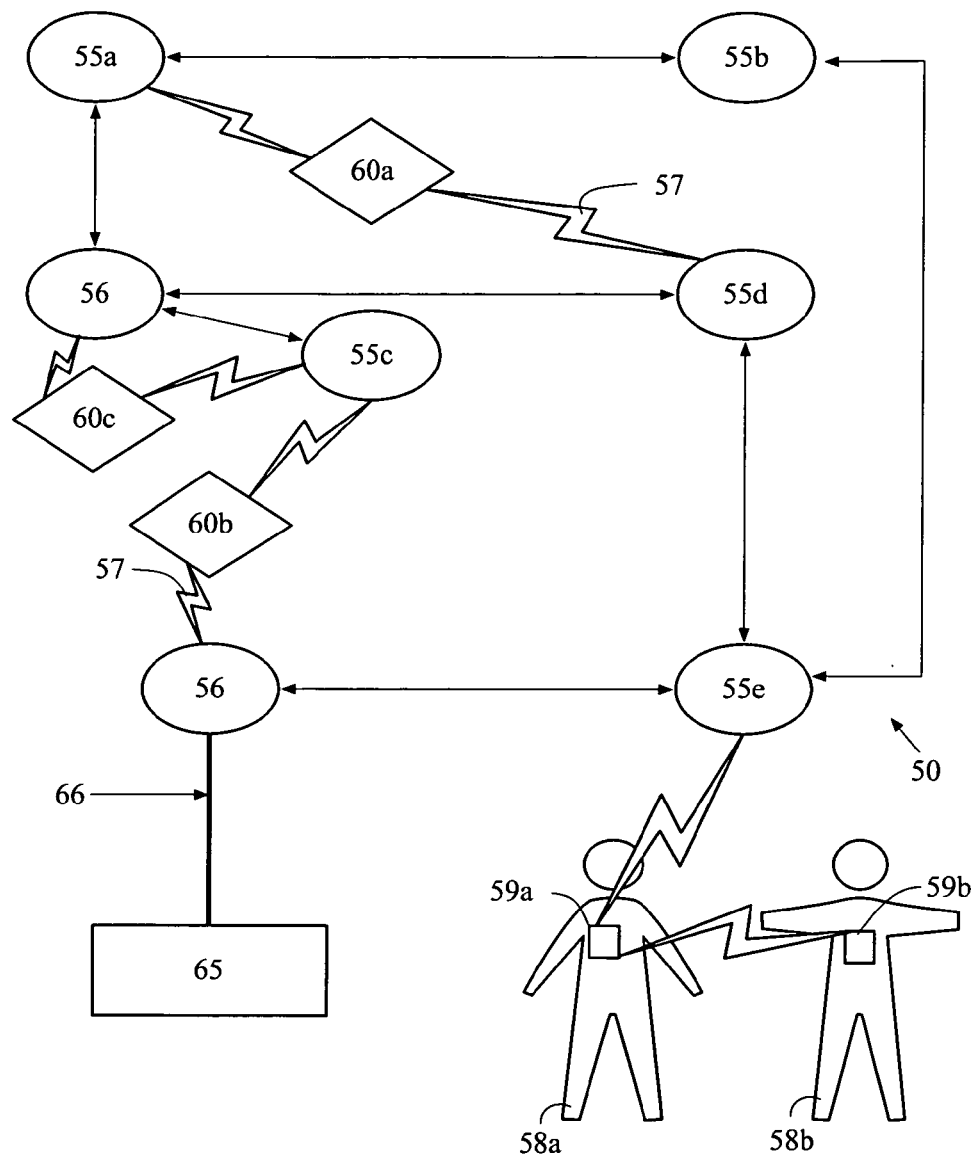
FIG. 1 is schematic view of a system for analyzing a near-field communication interaction.
Figure 2:
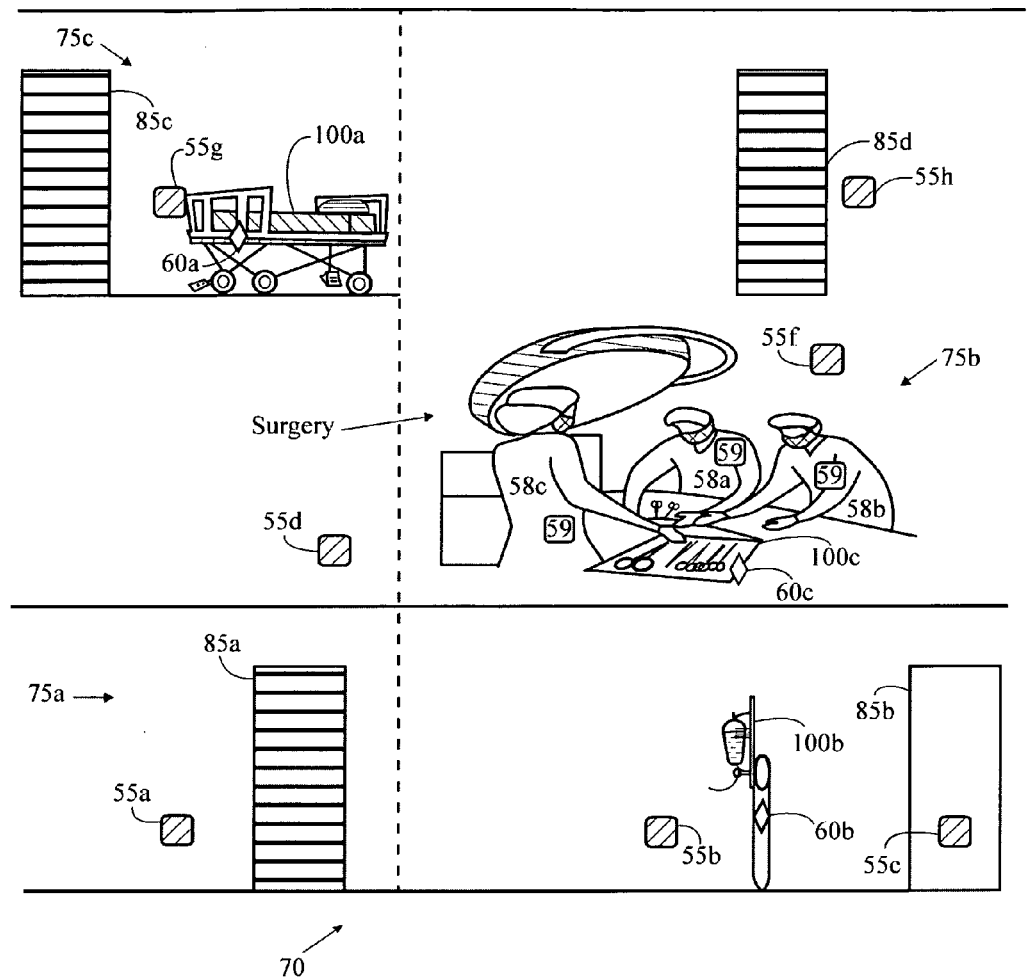
FIG. 2 is a multi-floor view of a facility employing a system for analyzing a near-field communication interaction.
Figure 3:
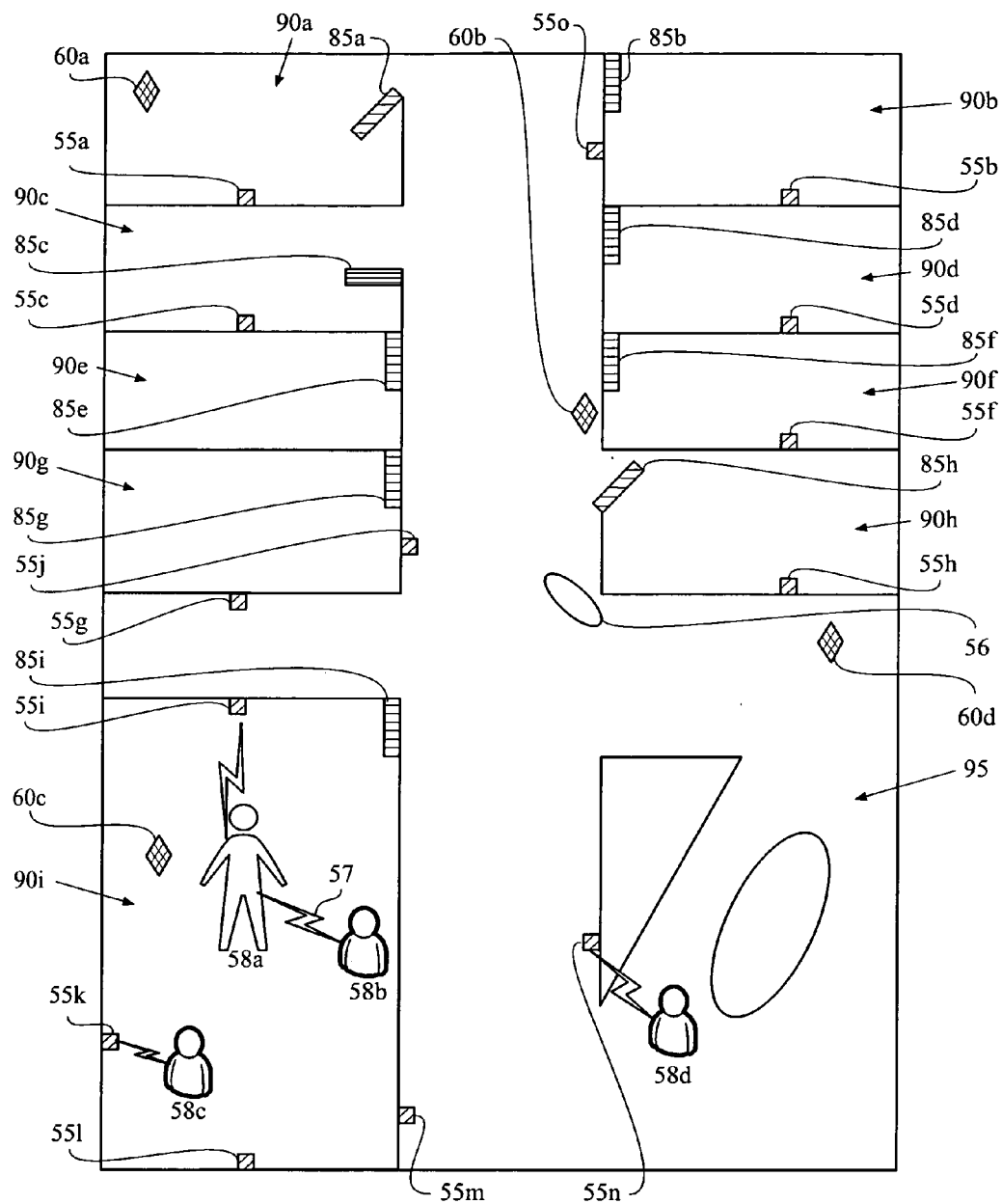
FIG. 3 is a floor plan view of a single floor in a facility employing the system for analyzing a near-field communication interaction.

As shown in FIGS. 1-3, a system for tracking objects within a facility is generally designated 50. The system 50 is capable of analyzing an interaction between objects, individuals 58 and/or objects 100. The system 50 preferably includes a plurality of sensors 55, a plurality of bridges 56, a plurality of near-field communication devices 59, a plurality of tags 60, and at least one information engine 65. The sensors 55 form a mesh network for receiving signals from the near-field communication devices 59 and tags 60. One example of the components of the system 50 is disclosed in U.S. Pat. No. 7,197,326, for a Wireless Position Location And Tracking System, which is hereby incorporated by reference in its entirety. A more specific example of the sensors 55 is disclosed in U.S. Pat. No. 7,324,824, for a Plug-In Network Appliance, which is hereby incorporated by reference in its entirety.

The system 50 is preferably employed at a facility 70 such as a business office, factory, home, hospital and/or government agency building. The system 50 is preferably utilized to track and locate various resources (including persons) positioned throughout the facility 70 in order to analyze near-field communication interactions. The near-field communication devices 59 and tags 60 preferably continuously transmit signals on a predetermined time cycle, and these signals are received by sensors 55 positioned throughout the facility 70. Alternatively, the tags 60 and near-field communication devices 59 transmit signals in a random, ad-hoc or dynamic manner, and these signals are received by the sensors 55 positioned throughout the facility 70. The sensors 55 transmit the data from the near-field communication devices 59 and tags 60 to a bridge 56 for transmission to the information engine 65. If a sensor 55 is unable to transmit to a bridge 56, the sensor 55 may transmit to another sensor 55 in a mesh network for eventual transmission to a bridge 56. In a preferred embodiment, a transmission may be sent from a transmission distance of six sensors 55 from a bridge 56. Alternatively, a transmission is sent from a transmission distance ranging from ten to twenty sensors 55 from a bridge 56. The information engine 65 preferably continuously receives transmissions from the mesh network formed by the sensors 55 via the bridges 56 concerning the movement of persons 58 bearing a near-field communication device 59 and/or devices 100 bearing a tag 60 within the facility 70. The information engine 65 processes the transmissions from the sensors 55 and calculates a real-time position for each of the objects, persons 58 bearing a near-field communication device 59 or objects 100 bearing a tag 60, within the facility 70. The real-time location information for each of the objects is preferably displayed on an image of a floor plan of the facility 70, or if the facility 70 has multiple floors, then on the floor plan images of the floors of the facility 70. The floor plan image may be used with a graphical user interface of a computer, personal digital assistant, or the like so that an individual of the facility 70 is able to quickly locate objects 100 within the facility 70.

As shown in FIG. 1, the system 50 utilizes sensors 55 to monitor and identify the real-time position of individuals bearing or integrated with communication devices 59. The sensors 55a-f preferably wirelessly communicate with each other (shown as double arrow lines) and with an information engine 65 through a wired connection 66 via at least one bridge 56, such as disclosed in the above-mentioned U.S. Pat. No. 7,324,824 for a Plug-In Network Appliance. The near-field communication devices 59 and tags 60 preferably transmit wireless signals 57 which are received by the sensors 55a-e, which then transmit signals to bridges 56 for eventual transmission to the information engine 65. The information engine 65 is preferably located on-site at the facility 70. However, the system 50 may also include an off-site information engine 65, not shown.

In a preferred embodiment, the near-field communication device 59 preferably operates at a short range communication format of magnetic induction, 9 kHz, <125 kHz, 125 kHz RFID, 13.56 MHz, 433 MHz, 433 MHz RFID, and 900 MHz RFID, and preferably at a bit rate of less 256 kilobits per second or approximately 426 kilobits per second. The communication format is preferably IEEE Standard 802.15.4. Further, the near-field communication device 59 also operates using a medium range communication format. The medium range communication format can include ZIGBEE, BLUETOOTH, BLUETOOTH low energy, WiFi, Low-power WiFi, Ultrasound and Infrared communication formats. Those skilled in the pertinent art will recognize that other communication formats may be used with departing from the scope and spirit of the present invention. The medium range communication format also allows the near-field communication device 59 to communicate with the sensors 55 to transmit interaction information.

In a preferred embodiment, the tag 60 preferably transmits a radio frequency signal of approximately 2.48 GigaHertz ("GHz"). The tags 60 may be constructed with an asset theft protection system such as disclosed in Baranowski et al., U.S. Pat. No. 7,443,297 for a Wireless Tracking System And Method With Optical Tag Removal Detection, which is hereby incorporated by reference in its entirety. The tags 60 and near-field communication devices 59 may be designed to avoid multipath errors such as disclosed in Nierenberg et al., U.S. Pat. No. 7,504,928 for a Wireless Tracking System And Method Utilizing Tags With Variable Power Level Transmissions, and Caliri et al., U.S. Patent Publication Number 2008/0012767 for a Wireless Tracking System And Method With Multipath Error Mitigation, both of which are hereby incorporated by reference in their entireties.

As shown in FIGS. 2-3, the facility 70 is depicted as a hospital. The facility 70 has multiple floors 75a-c. Each floor 75a, 75b and 75c has multiple rooms 90a-i, with each room 90 accessible through a door 85. Positioned throughout the facility 70 are sensors 55a-o for obtaining readings from communication devices 59 and tags 60 attached to people or objects. A bridge 56 is also shown for receiving transmissions from the sensors 55 for forwarding to the information engine 65. For example, as shown in FIG. 2, the system 50 determines that individuals 58a, 58b and 58c are located in a surgery room and are using device 100c, which is a surgical kit. The information engine 65 analyzes the interaction by monitoring the duration of the interaction, the devices 100 utilized, the location of the interaction (surgery), the previous location of the individuals 58 (possibly a surgical prep room) and additional factors.

In another example, as shown in FIG. 3, individuals 58a, 58b and 58c are located in a patient's room and are using a medical object with an attached tag 60c, which is a patient monitoring unit. In this example, individual 58a is a patient, individual 58b is a physician, and individual 58c is a nurse. The near-field communication device 59 of each individual 58a, 58b and 58c communicates with the other near-field communication devices 59 using a short range communication format as discussed above. In such a situation, each near-field communication device 59 registers the short range beacons transmitted by other near-field communication devices 59. Additionally, interaction information may be transferred between the near-field communication devices 59 using a medium range communication format as discussed above. Further, one, two or all of the near-field communication devices 59 transfer interaction information to at least one sensor 55 using a medium range communication format. The sensor 55 then transmits the interaction information to an information engine 65, preferably using a mesh network. The information engine 65 analyzes the near-field communication interaction information received by the sensor 55 by monitoring the duration of the near-field communication interaction, the objects 100 utilized, the location of the near-field communication interaction (patient's room), the previous location of the individuals 58 and additional factors. The information engine 65 preferably uses this data to generate billing information for the patient.

Figure 4:
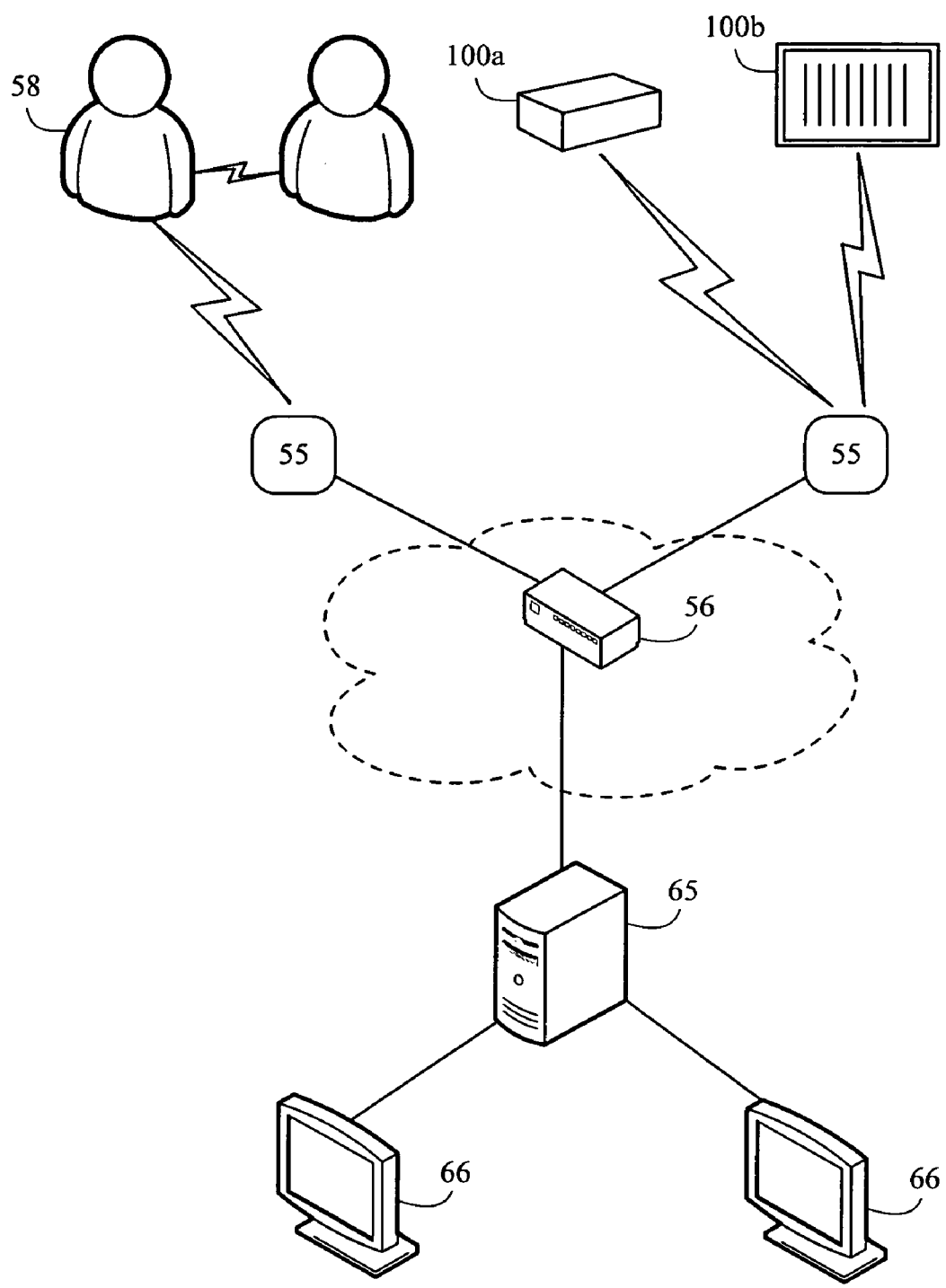
FIG. 4 is a block diagram of a flow of information utilizing a system for analyzing a near-field communication interaction.

FIG. 4 illustrates a preferred architecture of the system 50. For description purposes, the information providers are set forth on one side of the network and the operations is set forth on the other side of the network. However, those skilled in the pertinent art will recognize that the illustrated architecture of the system 50 is not meant to limit any physical relationship between information providers and operations. In fact, an individual 58 could be tracked while accessing information from an object 100 such as a computer 66 in operations. The information providers include individuals 58 that wear near-field communication devices 59, equipment 100a bearing tags 60, sterilizable equipment 100b bearing sterilizable tags 60, and the like. A description of sterilizable tags 60 and system is found in Caliri et al., U.S. Pat. No. 7,636,046 for Wireless Tracking System And Method With Extreme Temperature Resistant Tag, which is hereby incorporated by reference in its entirety. Another description of a sterilizable tag 60 and system is found in Perkins et al., U.S. Pat. No. 7,701,334 for Wireless Tracking System And Method For Sterilizable Object, which is hereby incorporated by reference in its entirety. A bridge 56 acts as an intermediary between the information providers and operations. The bridge 56 communicates information to the information engine 65 which analyzes the information to determine an interaction information between individuals for access through an enterprise local area network for display on computers 66 or other graphical user interface devices.

Figure 5:
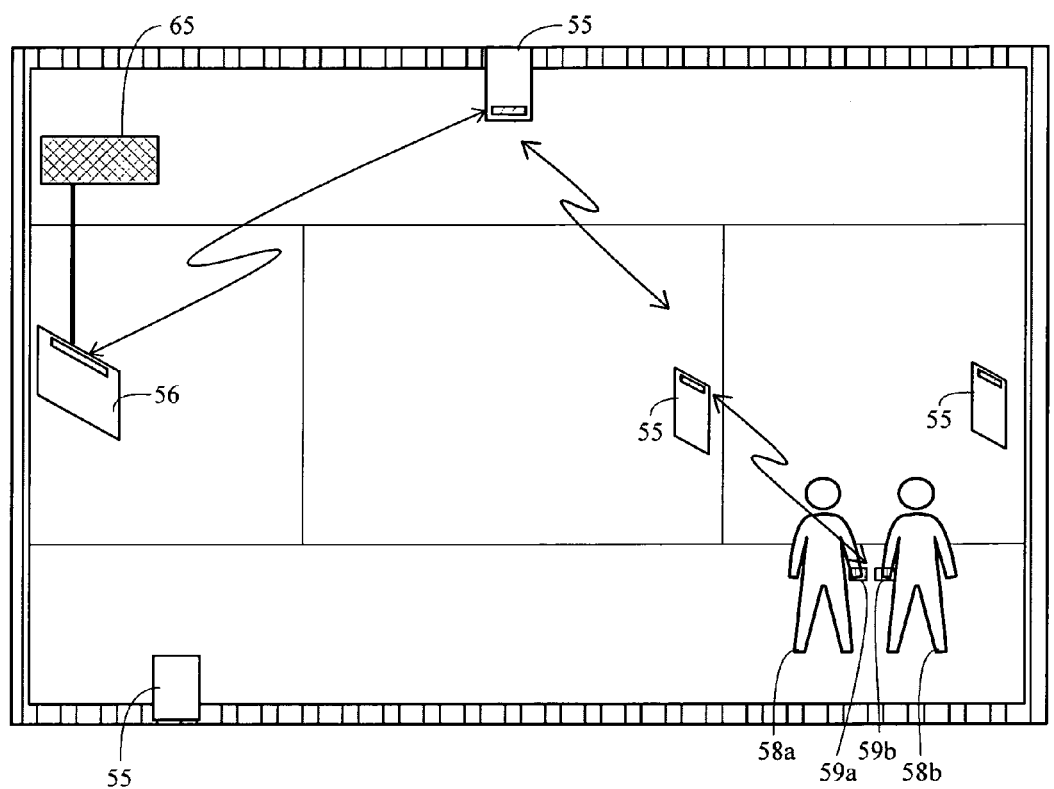
FIG. 5 is a block diagram of a flow of information utilizing a system for analyzing a near-field communication interaction.

A block diagram of a system utilizing near-field communication is illustrated in FIG. 5. In FIG. 5, two individuals 58a and 58b are in proximity in order to "mash-up" and have a valid near-field communication interaction with each individual's near-field communication devices 59a and 59b using a short range communication format as discussed above. A signal is transmitted from one of the individuals 58a near communication device 59a to a sensor 55 of a mesh network utilizing a medium range communication format as discussed above. The signal contains information pertaining to the near-field communication interaction. The sensor 55 transmits the signal through the mesh network to a bridge 56 for further transmission to an information processing engine 65.

Figure 5C:
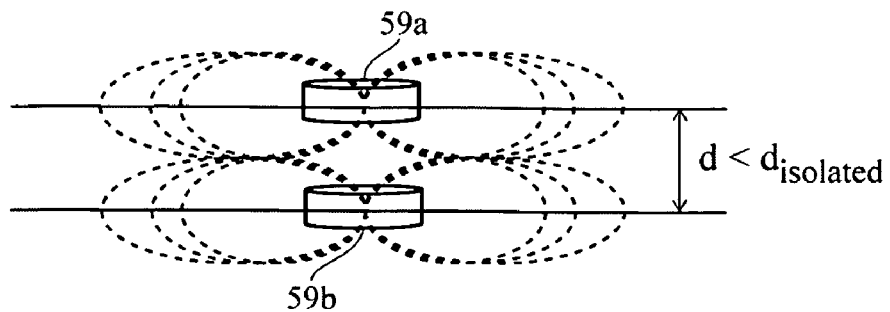
FIG. 5C is an illustration of a valid near-field link between near-field communication devices.
Figure 5B:
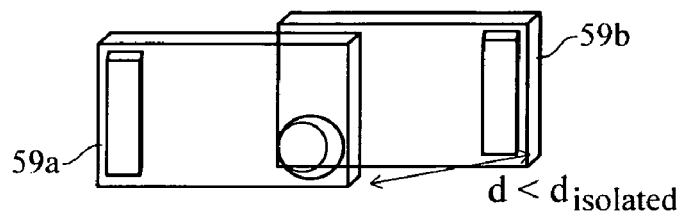
FIG. 5B is an illustration of a valid near-field link between near-field communication devices.
Figure 5A:
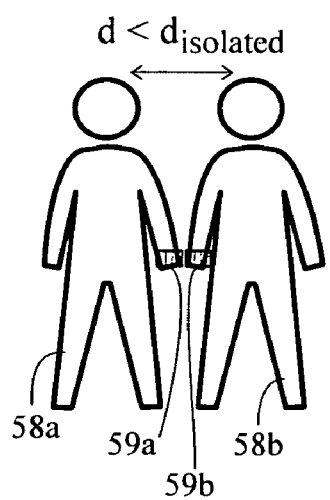
FIG. 5A is an illustration of a valid near-field link between near-field communication devices.

FIGS. 5A, 5B and 5C illustrate a valid near field communication link which occurs when the two near-field communication devices 59a and 59b are within a predetermined distance of each other (d<d isolated). Preferably the distance is ten centimeters or less. Most preferably there is a physical touch between the two near field communication devices. Requiring such proximity allows for power savings since the transmission field for each of the near field communication devices 59a and 59b is a minimal amount. If the near field communication device 59 were to transmit using a typical RFID signal or BLUETOOTH signal, then the power consumption would be greater. Those skilled in the art will recognize that the tag 60 and near field communication device 59 may be the same physical device with circuitry for both applications.

Figure 6B:
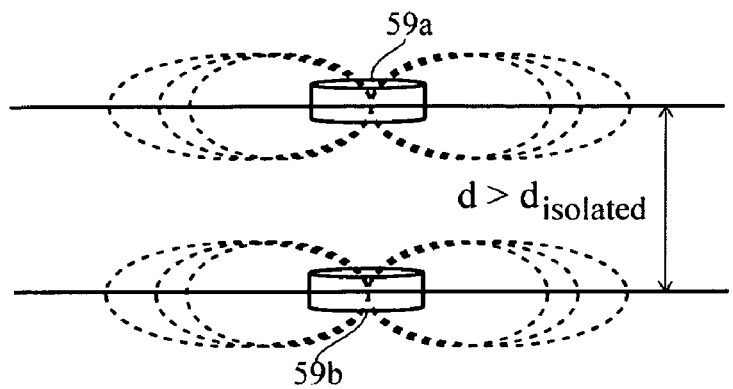
FIG. 6B is an illustration of a failed near-field link between near-field communication devices due to a distance between near-field communication devices.
Figure 6A:
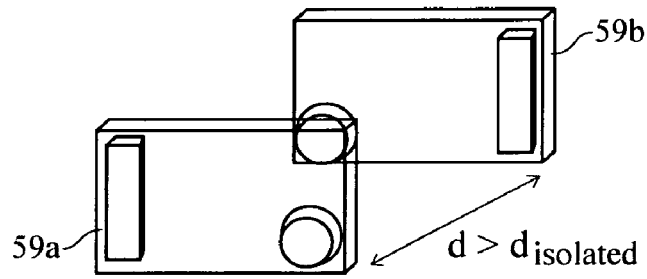
FIG. 6A is an illustration of a failed near-field link between near-field communication devices due to a distance between near-field communication devices.
Figure 6:
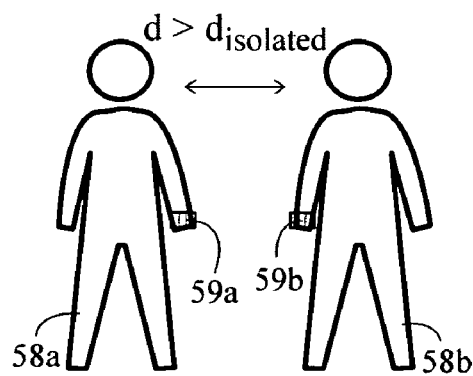
FIG. 6 is an illustration of a failed near-field link between near-field communication devices due to a distance between near-field communication devices.

FIGS. 6, 6A and 6B illustrate an unsuccessful near-filed communication link. In this situation, the two near-field communication devices 59a and 59b are not within a predetermined distance of each other (d>d isolated). Preferably, the distance is more than ten centimeters. In such a situation, there is no near field communication interaction. Thus, even though the near-field communication devices 59a and 59b are transmitting signal beacons, the individuals 58a and 58b are too far apart to detect a beacon signal from the other near-field communication device 59.

Figure 7:
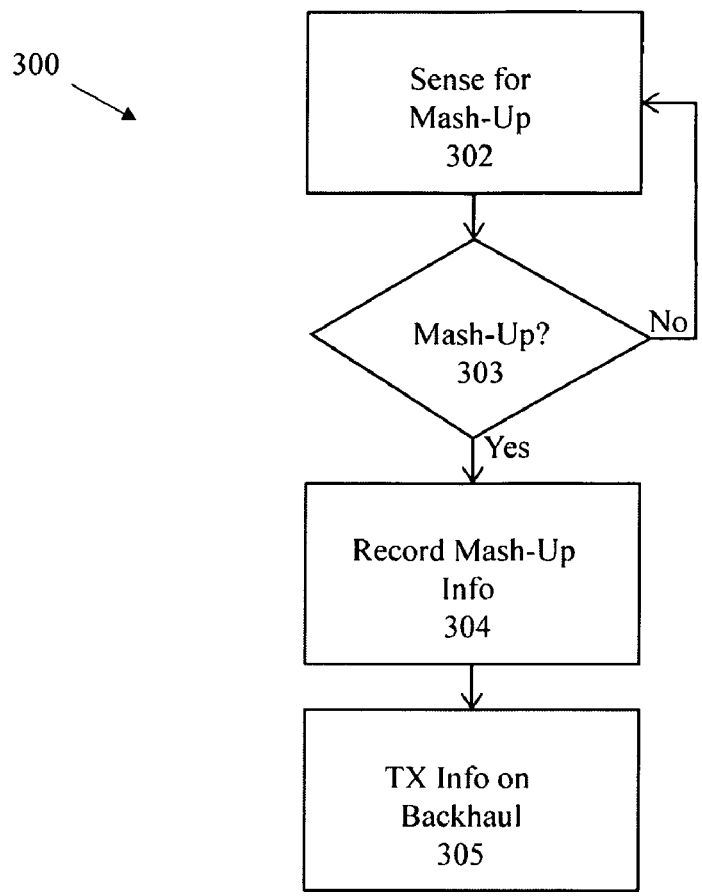
FIG. 7 is a flow chart of a method for analyzing a near-field communication interaction.

A method 300 utilizing near field communication is shown in FIG. 7. At block 302, a sensor 55 senses for a near field communication interaction ("mash-up") between at least two near-field communication devices 59. At a decision block 303, if no near field communication interaction is detected, then the sensor 55 continues to search for a near field communication interaction at block 302. However, if a near field communication interaction is detected by the sensor 55 at decision block 303, the near field communication interaction is recorded at block 304. Next, at block 305, data for the near field communication interaction is transmitted over the mesh network.

The near-field communication device 59 preferably includes a microcontroller, a first transceiver for transmitting at the short range communication format, a second transceiver for transmitting at the medium range communication format, a memory, and a power supply. The transmissions are transmitted through the transceivers. The power supply provides power to the components of the near-field communication device 59. All of the components are preferably contained within a housing. A tag 60 preferably has the same components and structure of the near-field communication device 59 except the tag 60 preferably only operates using the medium range communication format.

Figure 8:
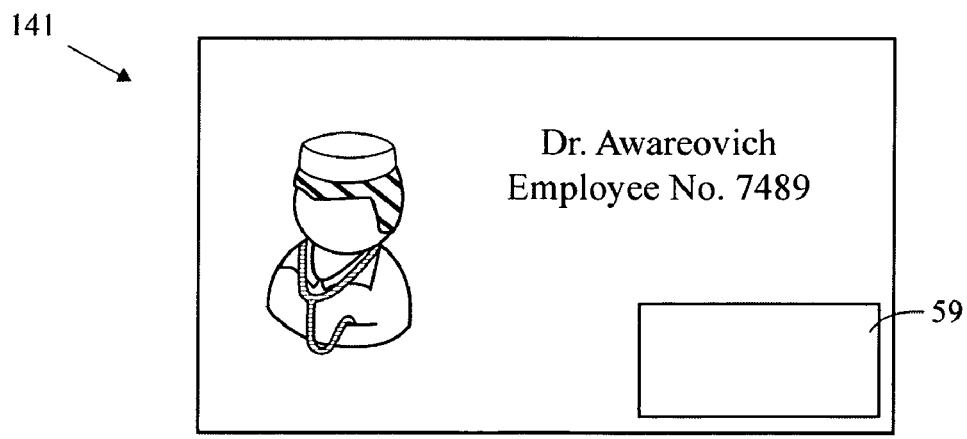
FIG. 8 is a plan view of an identification badge containing a communication device.

As shown in FIG. 8, an identification badge 141 is preferably utilized as a support for a near-field communication device 59 for a person 58. Alternatively, the identification badge 141 is the near-field communication device 59.

In one embodiment, the near-field communication interaction is utilized to authenticate a bearer of a near-field communication device 59 for access to at least one of or a combination of a computer, medical equipment, a protected area of the facility, a medication drawer, or a patient's room. For example, an individual 58 bearing the near-field communication device 59 is a physician and the physician 58 is granted access to a patient's room through a near-field communication interaction with a near-field communication device 59 on a door of the patient's room. In one example, the patient has a highly contagious disease and the tracking of access to the patient's room allows a hospital to know who has been exposed to the patient.

In another embodiment, the near-field communication interaction is utilized to track proper hand washing at a hospital. In this example, a near-field device 59 is positioned near a hand washing station for sterilizing hospital personal prior to surgery or similar procedures that require sterilization. When a bearer of a near field device 59 sterilizes his/her hands at the station, the interaction of the near-field devices 59 is recorded and transmitted to a sensor 55 for recordation at an information engine 65. In this manner, the hospital has a record to demonstrate that proper sterilization was performed prior to surgery or similar procedure requiring sterilization.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. A system utilizing near-field communications, the system comprising:
a mesh network comprising a plurality of sensors located in a facility for infrastructure-based real-time location tracking of objects and users in the facility, each of the plurality of sensors communicating with other sensors of the plurality of sensors utilizing a medium range wireless communication format, wherein each of the plurality of sensors operates in a geo-spatially fixed physical location in the facility;
a plurality of near-field communication devices, each of the plurality of near-field communication devices operating on a low power short-range wireless communication format and a medium range wireless communication format which is different than the low-power short-range wireless communication format, each of the plurality of near-field communication devices comprising a transceiver for transferring interaction data from one near-field communication device to another near-field communication device when the near-field communication devices are within a predetermined distance of each other, and a transceiver for transmitting a signal to at least one of the plurality of sensors, the signal comprising the interaction data and positioning data; and
an information engine in communication with the mesh network, the information engine processing the interaction data and positioning data.

2. The system according to claim 1 wherein the near-field communication data comprises a number of previous interactions between the near-field communication devices within a predetermined time period.

3. The system according to claim 1 wherein a bearer of a near-field communication device is at least one of a medical professional, a patient, an asset, an object, an area of the facility, or a host for a tag.

4. The system according to claim 1 wherein the interaction data is used to authenticate a user for access to at least one of or a combination of a computer, a medical equipment, a protected area of the facility, a medication drawer, or a patient's room.

5. The system according to claim 1 wherein the interaction data comprises at least one of or a combination of a previous location of the first bearer, a previous location of the second bearer, a current location of the first bearer, a current location of the second bearer, and a number of other objects located near the interaction.

6. A system for determining a business relationship between individuals within a facility, the system comprising:
a plurality of first near-field communication devices, each of the plurality of first near-field communication devices having bearer of the near-field communication device, each of the plurality of first near-field communication devices operating on a low power short-range wireless communication format and a medium range wireless communication format which is different than the low-power short-range wireless communication format;
a plurality of second near-field communication devices, each of the plurality of second near-field communication devices representing an object, each of the plurality of second near-field communication devices operating on a low power short-range wireless communication format and a medium range wireless communication format which is different than the low-power short-range wireless communication format;
a mesh network comprising a plurality of sensors located in a facility for infrastructure-based real-time location tracking of objects and users in the facility, each of the plurality of sensors communicating with other sensors of the plurality of sensors utilizing a medium range wireless communication format, wherein each of the plurality of sensors operates in a geo-spatially fixed physical location in the facility; and
an information engine in communication with the mesh network, the information engine obtaining data on a near-field communication interaction between either plurality of first near-field communication devices or at least one first near-field communication devices and a second object, the near-field communication interaction comprising a position location of the interaction and a duration of the interaction.

7. The system according to claim 6 wherein the second object is fixed or mobile.

8. The system according to claim 6 wherein the near-field communication data comprises a number of previous interactions between the near-field communication devices within a predetermined time period.

9. The system according to claim 6 wherein a bearer of a near-field communication device is at least one of a medical professional, a patient, an asset, an object, an area of the facility, or a host for a tag.

10. The system according to claim 6 wherein a near-field communication interaction occurs when the near-field communication devices are within a predetermined distance of each other.

11. The system according to claim 6 wherein the near-field communication interaction data further comprises a number of previous interactions between the first person and the second person within a predetermined time period.

12. The system according to claim 6 wherein each of the first plurality of near-field communication devices is mounted on a corresponding identification card or is an identification card.

13. The system according to claim 6 wherein the near-field communication interaction data further comprises at least one of or a combination of a previous location of the first object, a current location of the first object, a previous location of the second object, a current location of the second object, and the number of other objects located near the interaction.

14. A method for determining a business relationship between individuals within a facility, the method comprising:
transmitting a signal from a first near-field communication device associated with a first person, the first near-field communication device operating on a low power short-range wireless communication format and a medium range wireless communication format which is different than the low-power short-range wireless communication format;
receiving the signal from first near-field communication device at a second near-field communication device associated with a second person, the signal sent on a low power short-range wireless communication format, the second near-field communication device operating on a low power short-range wireless communication format and a medium range wireless communication format which is different than the low-power short-range wireless communication format;
determining that a near-field communication interaction is occurring between the first person and the second person based on the signal;
transmitting a signal using the medium range wireless communication format to a mesh network for transmission to an information engine;
determining a business relationship between the first person and the second person based on at least one of a plurality of factors comprising a position location of the interaction, a duration of the interaction, a previous location of the first person prior to the interaction, a previous location of the second person prior to the interaction and the number of other persons at the interaction.

15. The method according to claim 14 wherein the plurality of factors further comprises a position designation of the first person, a number of previous interactions between the first person and the second person within a predetermined time period, and a position designation of the second person.

16. The method according to claim 14 further comprising receiving a signal from the first near-field communication device at a mesh network established within the facility.

17. The method according to claim 14 wherein a near-field communication interaction occurs when the near-field communication devices are within ten centimeters of each other.

* * * * *